(12) United States Patent
Pfrengle

(10) Patent No.: US 6,284,762 B1
(45) Date of Patent: Sep. 4, 2001

(54) FUNGICIDAL 6-(2-HALO-4-ALKOXYPHENYL)-TRIAZOLOPYRIMIDINES

(75) Inventor: Waldemar Pfrengle, Seibersbach (DE)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/272,917

(22) Filed: Mar. 19, 1999

Related U.S. Application Data

(63) Continuation of application No. PCT/US98/05615, filed on Mar. 23, 1998.
(60) Provisional application No. 60/101,768, filed on Sep. 25, 1998.

(51) Int. Cl.[7] .......................... A01N 43/90; C07D 487/22
(52) U.S. Cl. ........................... 514/258; 540/600; 544/263
(58) Field of Search ..................... 544/263; 514/258; 540/600

(56) References Cited

U.S. PATENT DOCUMENTS 5,593,996 * 1/1997 Pees et al. ........................... 544/263
5,854,252 * 12/1998 Pees et al. ........................... 544/263

FOREIGN PATENT DOCUMENTS 0 550 113 * 7/1993 (EP) .

* cited by examiner

Primary Examiner—Mukund J. Shah
Assistant Examiner—Venkataraman Balasubramanian
(74) Attorney, Agent, or Firm—Barbara V. Maurer

(57) ABSTRACT

The novel compounds of formula I:

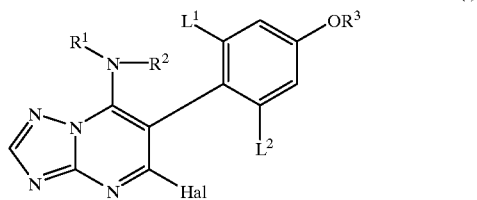

($R^1$, $R^2$, $R^3$, $L^1$, $L^2$ and Hal are defined in the specification) show selective fungicidal activity. These compounds may be processed with carriers, and optionally an adjuvant, to produce fungicidal compositions.

8 Claims, No Drawings

FUNGICIDAL 6-(2-HALO-4-ALKOXYPHENYL)-TRIAZOLOPYRIMIDINES

This application claims priority from copending provisional application(s) Ser. No. 60/101,768 filed on Sep. 25, 1998, which is a continuation of PCT/US98/05615 filed Mar. 23, 1998.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

U.S. Pat. No. 5,593,996 embraces compounds of the formula in which $R^1$ represents an optionally substituted alkyl, alkenyl, alkadienyl,

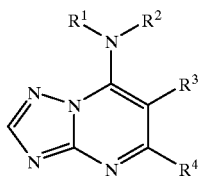

cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen or an alkyl group. Thus, compounds in which $R^3$ is a trichlorophenyl group are generally covered by this patent application. These compounds are said to be active against fungi which are members of the ascomycetes class such as *Venturia inaequalis* and of the hyphomycetes class such as *Alternaria solani* and *Botrytis cinerea*. However, there is no single compound disclosed in which $R^3$ is a 2-halo-4-alkoxyphenyl group.

SUMMARY OF THE INVENTION

The present invention provides a compound of formula I

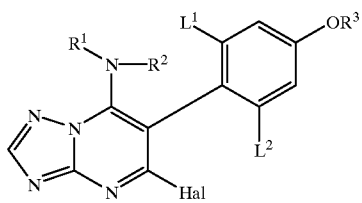

(I)

in which $R^1$ and $R^2$ each independently represent a hydrogen atom or an optionally substituted alkyl, alkenyl, alkynyl, alkadienyl, haloalkyl, aryl, heteroaryl, cycloalkyl, bicycloalkyl or heterocyclyl group, or $R^1$ and $R^2$ together with the interjacent nitrogen atom represent an optionally substituted heterocyclic ring, $R^3$ represents an alkyl, alkenyl, alkynyl, phenylalkyl, alkoxyalkyl, polyalkoxyalkyl, phenyl or haloalkyl group, $L^1$ represents a hydrogen, fluorine or chlorine atom, $L^2$ represents a fluorine or chlorine atom, and Hal represents a halogen atom.

The new compounds show excellent fungicidal activity in various crops, against a broad range of phytopathogenic fungi.

It is an object of the present invention to provide novel, selective fungicidal compounds.

It is also an object of the invention to provide methods for controlling an undesired fungus by contacting said plants with a fungicidally effective amount of the new compounds.

It is another object of the invention to provide fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

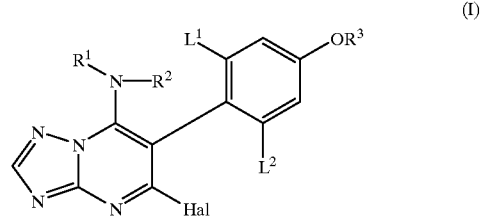

(I)

in which $R^1$, $R^2$, $R^3$, $L^1$, $L^2$ and Hal have the meaning given above for formula I show excellent fungicidal activity against a broad range of fungi.

As used herein, the term halogen atom may denote a bromine, iodine, chlorine or fluorine atom, and is preferably a bromine, chlorine or fluorine atom, more preferably a chlorine atom.

Optionally substituted moieties may be unsubstituted or have from one up to the maximal possible number of substituents. Typically, 0 to 2 substituents are present.

The terms alkyl, alkenyl, alkynyl, alkadienyl, as used herein with respect to a radical or moiety, refer to a straight or branched chain radical or moiety. Suitably, such radicals have up to 10, and preferably up to 6 carbon atoms. Suitably, an alkyl moiety has from 1 to 6 carbon atoms, preferably from 1 to 3 carbon atoms. A preferred alkyl moiety is an ethyl or especially a methyl group. Suitably, an alkenyl moiety has from 2 to 6 carbon atoms. A preferred alkenyl moiety is allyl, 2-methylallyl, 3-methylbut-2-enyl or 2-methylbut-3-enyl group.

Unless otherwise stated herein, the terms alkoxyalkyl, polyalkoxyalkyl as used herein with respect to a radical or moiety refer to a straight or branched chain radical or moiety having up to 16, in particular up to 10 carbon atoms. Suitably any alkyl moiety of such alkoxyalkyl or polyalkoxyalkyl groups has from 1 to 6 carbon atoms, preferably from 1 to 3 carbon atoms. A preferred alkoxyalkyl moiety is a methoxyalkyl, especially a 2-methoxyethyl or 2-methoxypropyl group. A preferred polyalkoxyalkyl moiety is a dialkoxyalkyl moiety such as 2-methoxyethoxyalkyl or 2-ethoxyethoxyalkyl especially a 2-(2-methoxyethoxy)-ethyl or a 2-(2-ethoxyethoxy)-ethyl group. Suitably an alkenyl moiety has from 2 to 6 carbon atoms. A preferred alkenyl moiety is an allyl, 2-methylallyl, 3-methylbut-2-enyl or 2-methylbut-3-enyl group.

The term aryl, as used herein with respect to a radical or moiety, refers to an aryl group having 6, 10 or 14 carbon atoms, preferably 6 or 10 carbon atoms, in particular phenyl optionally substituted by one or more halogen atoms, nitro, cyano, alkyl, preferably $C_{1-6}$ alkyl, and/or alkoxy, preferably $C_{1-6}$ alkoxy.

The term heteroaryl, as used herein with respect to a radical or moiety, refers to a heteroaryl group having 5 or 6 ring atoms selected from carbon, nitrogen, oxygen and sulphur, at least one of which is nitrogen, oxygen or sulphur.

The term cycloalkyl, as used herein with respect to a radical or moiety, refers to a cycloalkyl group having 3 to 8 carbon atoms, preferably 5 to 7 carbon atoms, in particular cyclohexyl optionally substituted by one or more halogen atoms, nitro, cyano, alkyl, preferably $C_{1-6}$ alkyl, and/or alkoxy, preferably $C_{1-6}$ alkoxy.

Unless otherwise stated herein, the term heterocyclyl, as used herein with respect to a radical or moiety, refers to a saturated heterocyclyl group having 5 or 6 ring atoms selected from carbon, nitrogen, oxygen and sulphur, at least one of which is nitrogen, oxygen or sulphur, optionally substituted by one or more halogen atoms, preferably fluorine, nitro, cyano, alkyl, preferably $C_{1-6}$ alkyl, alkoxy, preferably $C_{1-6}$ alkoxy, and/or haloalkyl, preferably $C_{1-6}$ haloalkyl. Preferred heterocyclyl groups include pyrrolodinyl, pyrrazolidin, piperidinyl, piperazinyl or morpholin-4-yl.

The term haloalkyl as used herein with respect to a radical or moiety refer to a straight or branched chain radical or moiety having up to 10 carbon and up to 21 halogen atoms, in particular up to 6 carbon and up to 13 halogen atoms. Suitably a haloalkyl moiety of this invention has from 1 to 6 carbon atoms, preferably from 1 to 3 carbon atoms. A preferred haloalkyl moiety is difluoromethyl, trifluoromethyl, 2-fluoroethyl, 2,2-difluoroethyl, 2,2,2-trifluoroethyl, 1,1,1-trifluoropro-2-yl or pentafluoroethyl group.

The invention especially related to compounds of formula I in which any alkyl part of the groups $R^1$, $R^2$ or $R^3$, which may be straight chained or branched, contains up to 10 carbon atoms, preferably up to 9 carbon atoms, more preferably up to 6 carbon atoms, any alkenyl or alkynyl part of the substituents $R^1$, $R^2$ or $R^3$ contains up to 10 carbon atoms, preferably up to 9 carbon atoms, more preferably up to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, and any aryl part of the substituent $R^1$ or $R^2$ contains 6, 10 or 14 carbon atoms, preferably 6 or 10 carbon atoms.

The term "optionally substituted" as used herein generally refers to a radical or moiety which is independently substituted by one or more halogen atoms or nitro, cyano, hydroxy, alkyl, preferably $C_{1-6}$ alkyl, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, trialkylsilyl, preferably tri-$C_{1-4}$ alkylsilyl, phenyl, halo- or dihalo-phenyl or pyridyl groups. Any alkyl, alkenyl or alkynyl group may be linear or branched.

In this invention, a 4- to 6-membered heterocyclic group may be any heterocyclic group with 4 to 6 ring atoms, interrupted by one or more heteroatoms selected from sulfur, nitrogen, and oxygen, preferably oxygen. A halogen atom suitably denotes a fluorine, chlorine or bromine atom.

Preferred embodiments of the invention include compounds of formula I in which $R^1$ represents a straight-chained or branched $C_{1-10}$ alkyl, in particular a branched $C_{3-10}$ alkyl group, a $C_{3-8}$ cycloalkyl, a $C_{3-8}$ cycloalkyl-$C_{1-6}$ alkyl, $C_{1-10}$ alkoxy-$C_{1-6}$ alkyl, a $C_{1-10}$ haloalkyl or a phenyl group optionally substituted by one to three halogen atoms or $C_{1-10}$ alkyl or $C_{1-10}$ alkoxy groups.

The invention especially relates to compounds of formula I in which $R^2$ represents a hydrogen atom, a $C_{1-10}$ alkyl or a $C_{1-10}$ haloalkyl group, in particular a hydrogen atom.

When $R^1$ is a $C_{1-10}$ haloalkyl group, preferably a polyfluorinated alkyl group, in particular a 2,2,2-trifluoroethyl, a 2-(1,1,1-trifluoropropyl) or a 2-(1,1,1-trifluorobutyl) group, $R^2$ preferably represents a hydrogen atom.

When $R^1$ is an optionally substituted $C_{3-8}$ cycloalkyl group, preferably a cyclopentyl or cyclohexyl group, $R^2$ preferably represents a hydrogen atom or $C_{1-6}$ alkyl group.

In another preferred embodiment of this invention, $R^1$ and $R^2$ together with the interjacent nitrogen atom form an optionally substituted heterocyclic ring, preferably an optionally substituted $C_{3-7}$ heterocyclic ring, in particular a pyrollidine, piperidine, tetrahydropyridine, in particular 1,2,3,6-tetrahydropyridine or azepane ring which is optionally substituted by one or more $C_{1-10}$ alkyl groups.

Included in the scope of the present invention are (R) and (S) isomers of compounds of formula I having a chiral center, and the racemates thereof, and salts, N-oxides and acid addition compounds thereof.

Excellent activity may be found in optically enriched compounds of formula I wherein $R^1$ represents a chiral group of formula —CH*(R')R", wherein R' and R" represent different alkyl or haloalkyl groups, in particular wherein R' represents a methyl group and R" represents a trifluoromethyl group.

$R^3$ preferably represents a straight-chained or primary hydrocarbyl moiety, which is branched in its 2-, 3 or 4-position with respect to its point of attachment to the oxygen atom, in particular a $C_{1-4}$ alkyl, a $C_{3-6}$ alkenyl, a $C_{3-6}$ alkynyl, a $C_{1-4}$ haloalkyl, a $C_{1-4}$ alkoxy-$C_{1-4}$ alkyl, a di($C_{1-4}$ alkoxy)-$C_{1-4}$ alkyl, or a benzyl group; most preferred is a methyl, ethyl, 3-methylbut-2-enyl, 2-methylbut-3-enyl, 2-fluoroethyl or 2,2,2-trifluoroethyl group.

$L^1$ preferably represents a hydrogen or a fluorine atom, in particular a fluorine atom; $L^2$ preferably represents a fluorine or a chlorine atom, in particular a fluorine atom.

The compounds according to formula I are oils, gums, or, crystalline solid materials. They have valuable fungicidal properties, in particular enhanced systemicity and enhanced fungicitoxity against rice diseases and powdery mildews compared to known fungicides. For example, they can be used in agriculture or related fields for the control of phytopathogenic fungi such as *Alternaria solani, Botrytis cinerea, Cercospora beticola, Cladosporium herbarum, Cochliobulus sativus, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Pyricularia oryzae, Rhizoctonia solani, Sclerotinia sclerotiorum* and *Uncinula necator*, in particular for the control of *Alternaria solani* and *Pyricularia oryzae*. The compounds of formula I according to the invention possess a high fungicidal activity within a wide concentration range and may be used in agriculture without any difficulties. Moreover, these compounds show enhanced control of fungi, in particular of rice blast disease, compared with conventional fungicides.

Good control of phytopathogenic fungi may be obtained by using a compound of formula I wherein:
Hal represents a chloro atom, and
$R^2$ represents a hydrogen atom.
Most preferred are the compounds of formula IA

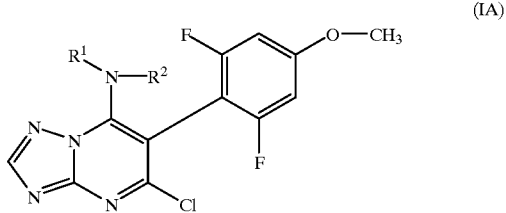

wherein
$R^1$ represents a straight-chained or branched $C_{1-10}$ alkyl, a straight-chained or branched $C_{3-10}$ alkenyl group, a $C_{3-8}$ cycloalkyl, a $C_{3-8}$ cycloalkyl-$C_{1-6}$ alkyl, $C_{1-10}$ alkoxy-$C_{1-6}$ alkyl or a $C_{1-10}$ haloalkyl group and $R^2$ represents a hydrogen atom; or
$R^1$ and $R^2$ together with the interjacent nitrogen atom form an optionally substituted $C_{4-7}$ heterocyclic ring.

Especially good control of phytopathogenic fungi may be obtained by using, for example, the following compounds of formula I:
5-chloro-7-(4-methylpiperidin-1-yl)-6-(2,6-difluoro-4-methoxyphenyl)-[1,2,4]triazolo[1,5-a]pyrimidine, 5-chloro-7-(N-isopropylamino)-6-(2,6-difluoro-4-methoxyphenyl)-[1,2,4]triazolo[1,5-a]pyrimidine, 5-chloro-7-(N-2,2,2-trifluoroethylamino)-6-(2,6-difluoro-4-methoxyphenyl)-[1,2,4]triazolo[1,5-a]pyrimidine, 5-chloro-7-[N-2-(1,1,1-trifluoropropyl)-amino]-6-(2,6-difluoro-4-methoxyphenyl)-[1,2,4]triazolo[1,5-a]pyrimidine, 5-chloro-7-amino-6-(2,6-difluoro-4-methoxyphenyl)-[1,2,4]triazolo[1,5-a]-pyrimidine, 5-chloro-7-[N-2-(1,1,1-trifluoropropyl)-amino]-6-(2,6-difluoro-4-isopropoxyphenyl)-[1,2,4]triazolo[1,5-a]pyrimidine, 5-chloro-7-[N-2-(1,1,1-trifluoropropyl)-amino]-6-(2,6-difluoro-4-ethoxyphenyl)-[1,2,4]triazolo[1,5-a]pyrimidine, 5-chloro-7-(N-cyclopentylamino)-6-(2,6-difluoro-4-methoxyphenyl)-[1,2,4]triazolo[1,5-a]pyrimidine, 5-chloro-7-(N,N-diethylamino)-6-(2,6-difluoro-4-methoxyphenyl)-[1,2,4]triazolo[1,5-a]-pyrimidine, 5-chloro-7-(N-but-2-ylamino)-6-(2,6-difluoro-4-methoxyphenyl)-[1,2,4]triazolo[1,5-a]pyrimidine, 5-chloro-7-(3,4-dehydropiperidin-1-yl)-6-(2,6-difluoro-4-methoxyphenyl)-[1,2,4]triazolo[1,5-a]pyrimidine, 5-chloro-7-N-morpholino-6-(2,6-difluoro-4-methoxyphenyl)-[1,2,4] triazolo[1,5-a]-pyrimidine, 5-chloro-7-N-thiomorpholino-6-(2,6-difluoro-4-methoxyphenyl)-[1,2,4]triazolo[1,5-a]pyrimidine, 5-chloro-7-azepan-1-yl-6-(2,6-difluoro-4-methoxyphenyl)-[1,2,4]triazolo[1,5-a]pyrimidine, 5-chloro-7-(N-ethyl-N-2-methylallylamino)-6-(2,6-difluoro-4-methoxyphenyl)-[1,2,4]triazolo[1,5-a]-pyrimidine, 5-chloro-7-(4-hydroxymethylpiperidin-1-yl)-6-(2,6-difluoro-4-methoxyphenyl)-[1,2,4]triazolo[1,5-a]pyrimidine,5-chloro-7-(4-fluoromethylpiperidin-1-yl)-6-(2,6-difluoro-4-methoxyphenyl)-[1,2,4]triazolo[1,5-a]pyrimidine, 5-chloro-7-(N-norborn-2-ylamino)-6-(2,6-difluoro-4-methoxyphenyl)-[1,2,4]triazolo[1,5-a]pyrimidine 5-chloro-7-(N-cyclopropylamino)-6-(2,6-difluoro-4-methoxyphenyl)-[1,2,4]triazolo[1,5-a]pyrimidine, 5-chloro-7-[N-2-(1,1,1-trifluoropropyl)-amino]-6-(2,6-difluoro-4-(2-fluoroethoxy)-phenyl)-[1,2,4]triazolo[1,5-a]-pyrimidine, (S)-5-chloro-7-[N-2-(1,1,1-trifluoropropyl)-amino]-6-(2,6-difluoro-4-methoxyphenyl)-[1,2,4]triazolo[1,5-a]pyrimidine, 5-chloro-7-[N-2-(1,1,1-trifluoropropyl)-amino]-6-(2,6-difluoro-4-(3-methylbut-2-enyloxy)-phenyl)-[1,2,4]triazolo[1,5-a]pyrimidine, 5-chloro-7-[N-2-(1,1,1-trifluoropropyl)-amino]-6-(2,6-difluoro-4-(2-methylbut-3-enyloxy)-phenyl)-[1,2,4]triazolo[1,5-a]pyrimidine, 5-chloro-7-[N-2-(1,1,1-trifluoropropyl)-amino]-6-(2,6-difluoro-4-(3-methylbutoxy)phenyl)-[1,2,4]triazolo[1,5-a]-pyrimidine, 5-chloro-7-[N-2-(1,1,1-trifluoropropyl)-amino]-6-(2,6-difluoro-4-benzyloxyphenyl)-[1,2,4]triazolo[1,5-a]pyrimidine, 5-chloro-7-[N-2-(1,1,1-trifluoropropyl)-amino]-6-(2,6-difluoro-4-[2-(2-ethoxy-ethoxy)-ethoxy]-phenyl)-[1,2,4]triazolo[1,5-a]pyrimidine, 5-chloro-7-[N-2-(1,1,1-trifluoropropyl)-amino]-6-(2,6-difluoro-4-[2-(2-methoxy-ethoxy)-ethoxy]-phenyl)-[1,2,4]triazolo[1,5-a]pyrimidine, 5-chloro-7-(N-isopropylamino)-6-(2,6-difluoro-4-ethoxyphenyl)-[1,2,4]triazolo[1,5-a]pyrimidine, 5-chloro-7-(N-2-methylallyl-N-ethylamino)-6-(2,6-difluoro-4-ethoxyphenyl)-[1,2,4]triazolo[1,5-a]pyrimidine, 5-chloro-7-(azepan-1-yl)-6-(2,6-difluoro-4-ethoxyphenyl)-[1,2,4]triazolo[1,5-a]pyrimidine, 5-chloro-7-[N-2-(1,1,1-trifluoropropyl)-amino]-6-(2,6-difluoro-4-(2,2,2-trimethylethoxy)-phenyl)-[1,2,4]triazolo[1,5-a]pyrimidine, 5-chloro-7-[N-2-(1,1,1-trifluoropropyl)-amino]-6-(2,6-difluoro-4-(2-methoxyethoxy)-phenyl)-[1,2,4]triazolo[1,5-a]-pyrimidine, 5-chloro-7-[N-2-(1,1,1-trifluoropropyl)-amino]-6-(2,6-difluoro-4-(2-methoxypropoxy)-phenyl)-[1,2,4]triazolo[1,5-a]pyrimidine, 5-chloro-7-[N-2-(1,1,1-trifluoropropyl)-amino]-6-(2,6-difluoro-4-but-2-enyloxyphenyl)-[1,2,4]triazolo[1,5-a]pyrimidine, and 5-chloro-7-[N-2-(1,1,1-trifluoropropyl)-amino]-6-(2,6-difluoro-4-(2,2,2-trifluoroethoxy)-phenyl)-[1,2,4]triazolo[1,5-a]pyrimidine.

The present invention further provides a process for the preparation of a compound of formula I as defined above which comprises treating a compound of the formula II

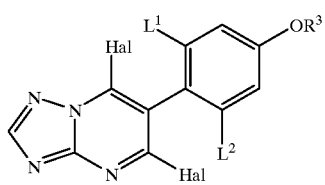

in which $R^3$, $L^1$, $L^2$ and Hal are as defined for formula I; with an amine of the formula III

in which $R^1$ and $R^2$ are as defined for formula I, to produce a compound of formula I.

Alternatively, the compounds of formula I can be prepared by a process which comprises treating a compound of the formula IV

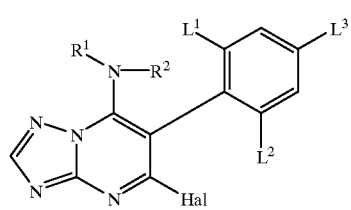

(IV)

in which $R^1$, $R^2$, $L^1$; $L^2$ and Hal are as hereinbefore defined and $L^3$ represents a leaving group, in particular a fluorine atom, with an alcohol of formula V $R^3$—OH         (V)

in the presence of a strong base.

Compounds of formula II are novel and may be prepared by reacting 3-amino-1,2,4-triazole with 2-(2-halo-4-alkoxyphenyl)-substituted malonic acid ester of formula VI,

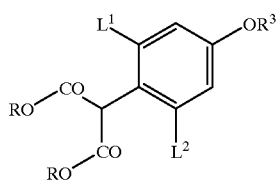

(VI)

wherein R represents alkyl, preferably $C_{1-6}$ alkyl, in particular methyl or ethyl, under alkaline conditions, preferably using high boiling tertiary amines as for example tri-n-butylamine.

The compounds of formula IV are preferably prepared by reaction of 2-halo-4-alkoxy-bromobenzene, in particular 1-bromo-2,6-difluoro-4-methoxybenzene with sodium dialkylmalonates in the presence of a copper(I) salt, a reaction analogous to that shown in J. Setsume et al. Chemistry Letters, pp. 367–370, 1981.

The resulting 5,7-dihydroxy-6-(2-halo-4-alkoxyphenyl)-triazolopyrimidine of formula VII

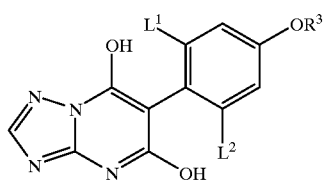

(VII)

is subsequently treated with a halogenating agent, preferably with a brominating or chlorinating agent, such as phosphorus oxybromide or phosphorus oxychloride, either neat or in the presence of a solvent and/or a base. The reaction is suitably carried out at a temperature in the range from about 0° C. to about 150° C., the preferred reaction temperature being from about 80° C. to about 125° C. as disclosed for example by EP 0 770 615.

Accordingly, the invention relates to the novel intermediates of formula II, in particular 5,7-dichloro-6-(2,6-difluoro-4-methoxyphenyl)-[1,2,4]triazolo[1,5-a]pyrimidine, to the dialkyl (2-halo-4-alkoxyphenyl)-malonates of formula VI, and to the novel intermediates of formula VII, especially 5,7-dihydroxy-6-(2,6-difluoro-4-methoxyphenyl)-[1,2,4]triazolo[1,5-a]pyrimidine.

The reaction between the 5,7-dihalo-6-(2-halo-4-alkoxyphenyl)-triazolopyrimidines of formula II and the amine of formula III is preferably carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene. The reaction is suitably carried out at a temperature in the approximate range from 0° C. to 70° C., the preferred reaction temperature being approximately from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The compounds of formula I may be used in cultivation of all plants where infection by phytopathogenic fungi is not desired, e.g. cereals, solanaceous crops, vegetables, legumes, apples, vine.

The invention further provides a fungicidal composition which comprises an active ingredient, which is at least one compound of formula I as defined above, and one or more carriers. A method of making such a composition is also within the scope of the invention. This method comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and, thus, compositions may comprise individual isomers or mixtures of isomers.

A composition according to the invention preferably contains from about 0.5% to about 95% by weight (w/w) of active ingredient.

A carrier in a composition according to the invention is any material with which the active ingredient is formulated to facilitate application to the locus to be treated (which may, for example, be a plant, seed, soil, or water in which a plant grows), or to facilitate storage, transport or handling. A carrier may be a solid or a liquid, including material which is normally a gas but which has been compressed to form a liquid.

The compositions of this invention may be manufactured into, e.g., emulsion or emulsifiable concentrates, solutions, oil in water emulsions, wettable powders, soluble powders, suspension concentrates, dusts, granules, water dispersible granules, micro-capsules, gels, tablets, aerosols and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application, such as spraying, atomizing, dispersing or pouring, may be chosen according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g.

n-octylpyrrolidone or cyclohexylpyrrolidone, epoxidized plant oil esters, e.g. methylated coconut or soybean oil ester, and water. Mixtures of different solvents are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to formula I to be formulated. Surfactants in this invention may also include mixtures of individual surfactants.

Wettable powders suitably contain about 5 to 90% w/w of active ingredient, and in addition to solid inert carrier, about 3 to 10% w/w of dispersing and wetting agents and about 0 to 10% w/w of stabilizer(s) and/or other additives such as penetrants or stickers. Dusts may be formulated as a dust concentrate having a similar composition to that of a wettable powder, but without a dispersant, and may be diluted in the field with further solid carrier to give a composition preferably containing about 0.5 to 10% w/w of active ingredient. Water dispersible granules and granules of the invention preferably have a size between about 0.15 mm and 2.0 mm and may be manufactured by a variety of techniques. These granules preferably contain about 0.5 to 90% w/w active ingredient and about 0 to 20% w/w of additives such as stabilizer, surfactants, slow release modifiers and binding agents. Emulsifiable concentrates of the invention suitably contain, in addition to a solvent or a mixture of solvents, about 1 to 80% w/v active ingredient, about 2 to 20% w/v emulsifiers and about 0 to 20% w/v of other additives such as stabilizers, penetrants and corrosion inhibitors. Suspension concentrates are preferably milled so as to obtain a stable, non-sedimenting flowable product and usually contain about 5 to 75% w/v active ingredient, about 0.5 to 15% w/v of dispersing agents, about 0.1 to 10% w/v of suspending agents such as protective colloids and thixotropic agents, about 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents.

Aqueous dispersions and emulsions, for example compositions obtained by diluting the formulated product according to the invention with water, also lie within the scope of the invention.

In one embodiment of the invention, to enhance the duration of the protective activity of the compounds of this invention, a carrier is used which provides slow release of the pesticidal compounds into the environment of a plant which is to be protected.

The biological activity of the active ingredient may be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added separately, e.g., to a spray tank together with the formulation containing the active ingredient.

As a commodity, the compositions preferably may be in a concentrated form, whereas the end user generally employs diluted compositions. The compositions may be diluted to a concentration down to about 0.001% of active ingredient. The doses usually are in the approximate range from 0.01 to 10 kg a.i./ha.

Examples of formulations according to the invention are:

| | Emulsion Concentrate (EC) | |
|---|---|---|
| Active Ingredient | Compound of Example 3 | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |
| | Suspension Concentrate (SC) | |
| Active Ingredient | Compound of Example 6 | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| | Wettable Powder (WP) | |
| Active Ingredient | Compound of Example 6 | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates) | 3% (w/w) |
| Carrier/Filler | Kaolin | 35% (w/w) |
| | Water Dispersible Granules (WG) | |
| Active Ingredient | Compound of Example 6 | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |

| | | |
|---|---|---|
| | -continued | |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products The compositions of this invention can be applied to the plants or their environment, either simultaneously with, or in succession with, other active substances. These other active substances may include fertilisers, agents which donate trace elements, or other preparations which influence plant growth. However, they also include selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these substances, optionally together with other carrier substances conventionally used in the art of formulation, including surfactants or other additives which promote application.

Furthermore, the other pesticide can have a synergistic effect on the pesticidal activity of the compound of formula I.

The other fungicidal compound can be, for example, one which is also capable of combating diseases of cereals (e.g. wheat) such as those caused by Erysipha, Puccinia, Septoria, Gibberella and Helminthosporium spp., seed and soil borne diseases and downy and powdery mildews on vines, early and late blight on solanaceous crops, and powdery mildew and scab on apples etc. These mixtures of fungicides can have a broader spectrum of activity than the compound of formula I alone. Furthermore, the other fungicide can have a synergistic effect on the fungicidal activities of the compound of formula I.

Examples of the other fungicidal compounds are alanycarb, aldimorph, ampropylfos, andoprim, anilazine, azaconazole, azafenidin, azoxystrobin, benalaxyl, benodanil, benomyl, benzamacril, bialaphos, biloxazol, binapacryl, biphenyl, bitertanol, blasticidin S, Bordeaux mixture, bromuconazole, bupirimate, butenachlor, buthiobate, captafol, captan, carbendazim, carboxin, carpropamid, carvone, chinomethionat, chlorbenzthiazon, chlorfenazol, chloroneb, chloropicrin, chlorothalonil, chlozolinate, clozylacon, copper-containing compounds such as copper oxychloride, and copper sulfate, cufraneb, cycloheximide, cymoxanil, cypofuram, cyproconazole, cyprodinil, cyprofuram, debacarb, dichlofluanid, dichlone, dichloran, dichlorophen, diclobutrazol, diclocymet, diclomezine, dicloran, diethofencarb, difenoconazole, difenzoquat, diflumetorim, dimefluazole, dimethirimol, dimethomorph, diniconazole, dinocap, diphenylamin, dipyrithione, ditalimfos, dithianon, dodemorph, dodine, drazoxolon, edifenphos, epoxiconazole, etaconazole, ethirimol, ethoxyquin, etridiazole, famoxadone, fenapanil, fenamidone, fenaminosulph, fenarimol, fenbuconazole, fenfuram, fenhexamid, fenitropan, fenpiclonil, fenpropidin, fenpropimorph, fentin, fentin acetate, fentin hydroxide, ferbam, ferimzone, fluazinam, fludioxonil, flumetover, fluoromid, fluquinconazole, flurprimidol, flusilazole, flusulfamide, flutolanil, flutriafol, folpet, fosetyl-aluminium, fuberidazole, furalaxyl, furametpyr, furcarbonil, furconazole-cis, furmecyclox, guazatine, hexachlorobenzol, hexaconazole, hydroxyisoxazole, hymexazole, IKF-916, imazalil, imibenconazole, iminoctadine, iodocarb, ipconazole, iprobenfos, iprodione, iprovalicarb, isoprothiolane, isovaledione, kasugamycin, RH-7281, kitazin P, kresoxim-methyl, mancozeb, maneb, mefenoxam, meferimzone, mepanipyrim, mepronil, metalaxyl, metconazole, methasulfocarb, methfuroxam, metiram, metomeclam, metominostrobon, metsulfovax, MON 65500, myclobutanil, myclozolin, neoasozin, nickel dimethyidithiocarbamate, nitrothalisopropyl, nuarimol, ofurace, organo mercury compounds, oxadixyl, oxamocarb, oxasulfuron, oxycarboxin, paclobutrazol, pefurazoate, penconazole, pencycuron, phenazineoxide, phosdiphen, phthalide, picoxystrobin, pimaricin, piperalin, polyoxin D, polyram, probenazole, prochloraz, procymidone, propamocarb, propiconazole, propineb, prothiocarb, pyracarbolid, pyrazophos, pyrifenox, pyrimethanil, pyroquilon, pyroxyfur, quinconazole, quinomethionate, quinoxyfen, quintozene, rabenazole, sipconazole, spiroxamine, SSF-126, SSF-129, streptomycin, sulfur, tebuconazole, tecloftalame, tecnazene, tetcyclacis, tetraconazole, thiabendazole, thicyofen, thifluzamide, thiophanate-methyl, thiram, tioxymid, tolclofosmethyl, tolylfluanid, triadimefon, triadimenol, triazbutil, triazoxide, trichlamid, tricyclazole, tridemorph, trifloxystrobin, triflumizole, triforine, triticonazole, uniconazol, validamycin A, vapam, vinclozolin, XRD-563, zarilamid, zineb, and ziram.

In addition, the formulations of the invention may contain at least one compound of formula I and any of the following classes of biological control agents: viruses, bacteria, nematodes, fungi, and other microorganisms which are suitable to control insects, weeds or plant diseases or to induce host resistance in the plants. Examples of such biological control agents are: *Bacillus thuringiensis, Vericillium lecanii, Autographica californica* NPV, *Beauvaria bassiana, Ampelomyces quisqualis, Bacilis subtilis,* Phycarine (a beta-1,3 glucan of marin origin extracted from brown algae available from Goemar—France), *Pseudomonas choloraraphis, Pseudomonas fluorescens, Steptomyces griseoviridis, Trichoderma harzianum,* and Trichobiol (a Trichoderma spp., available from Souza Cruz—Brazil).

Moreover, the formulations according to the invention may contain at least one compound of formula I and a chemical agent that induces systemic acquired resistance in plants, such as, for example, isonicotinic acid or derivatives thereof, 2,2-dichloro-3,3-dimethyl-cyclopropylcarboxylic acid or BION.

The compounds of formula I can be mixed with soil, peat or other rooting media for the protection of the plants against seed-borne, soil-borne or foliar fungal diseases.

The invention further includes the fungicidal use of a compound of the formula I as defined above, or a composition as defined above, and a method for combating fungus at a locus, which comprises treating the locus (which may be plants subject to or subjected to fungal attack, seeds of such plants or the medium in which such plants are growing or are to be grown) with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the indi-

13 vidual compound selected, and also a variety of external factors, such as climate, whose impact may be mitigated by the use of a suitable formulation.

The following examples further illustrate the present invention. It should be understood, however, that the invention is not limited solely to the particular examples given below.

EXAMPLE 1

Preparation of diethyl 2,6-difluoro-4-methoxyphenylmalonate Diethyl malonate (0.505 mol) is added to a mixture of sodium hydride (0.412 mol) and 1,4-dioxane (230 ml) at 40° C. within 3 hours. The mixture is stirred for 90 minutes at 60° C. and copper(I) bromide (0.402 mol) is added. A mixture of 2,6-difluoro-4-methoxybromobenzene (0.2 mol) and 1,4-dioxane (50 ml) is added. The reaction mixture is heated at 100° C. for 14 hours and cooled to 15° C. Hydrochloric acid (12N, 350 ml) is added slowly at 15 to 20° C. The organic phase is separated off and the aqueous phase is extracted with ethyl acetate (250 ml) and toluene (200 ml). The combined organic phases are concentrated in vacuo. The residue is filtered over silica gel, washed with petroleum ether/ethyl acetate (15:1) and the solvent is distilled off. The residue is distilled in vacuo to yield 44.8 g of the product as an oil, 128–136° C. at 0.018 mbar.

EXAMPLE 2

Preparation of 5,7-Dichloro-(2,6-difluoro-4-methoxyphenyl)-1,2,4-triazolo[1.5a]pyrimidine A mixture of 3-amino-1,2,4-triazole (0.111 mol), diethyl 2,6-difluoro-4-methoxyphenylmalonate (0.1 mol, obtained from Example 1) and tributylamine (26 ml) is heated at 180° C. and ethanol formed during the reaction is distilled off. Subsequently, the reaction mixture is cooled to ambient temperature and the excess of tributylamine is decanted off. The residue is diluted with dichloromethane washed with dilute hydrochloric acid and water and crystallized from diisopropylether to yield 51 g of the pure 5,7-dihydroxy-(2,6-difluoro-4-methoxyphenyl)-1,2,4-triazolo[1.5a]pyrimidine having a melting point of 276–281° C. Subsequently phosphorous oxychloride (60 ml) is added to 5,7-dihydroxy-(2,6-difluoro-4-methoxyphenyl)-1,2,4-triazolo[1.5a]pyrimidine (0.11 mol) within 30 minutes. The reaction mixture is heated with reflux for 6 hours. The excess of phosphorous oxychloride is distilled off and a mixture of water and dichloromethane is added slowly. The organic phase is separated, washed with a dilute sodium bicarbonate solution and water, dried, concentrated in vacuo and recrystallized from i-propanol to yield a light brown solid (57.4 g) having a melting point of 152–155° C.

EXAMPLE 3

Preparation of 5-chloro-(2,6-difluoro-4-methoxyphenyl)-7-(4-methylpiperid-1-yl)-1,2,4-triazolo[1.5a]pyrimidine A mixture of 4-methylpiperidine (1.4 mmoles), triethylamine (1.4 mmoles) and dichloromethane (10 ml) is added to a mixture of 5,7-dichloro-(2,6-difluoro-4-methoxyphenyl)-1,2,4-triazolo[1.5a]pyrimidine (1.4 mmoles) and dichloromethane (30 ml) under stirring. The reaction mixture is stirred 16 hours at room temperature, subsequently washed two times with 1 N hydrochloric acid and once with water. The organic layer is separated, dried with anhydrous sodium sulphate and the solvent is evaporated under reduced pressure. Treatment of the resulting light brown oil with tert.-butyl methyl ether (50 ml) yields white crystals having a melting point of 148° C.

EXAMPLE 4

Preparation of 5-dichloro-(2,6-difluoro-4-(2-methoxyethoxy)phenyl)-7-[(R,S)-1,1,1-trifluoroprop-2-ylamino]-1,2,4-triazolo[1.5a]pyrimidine To diethylene glycol monomethyl ether (0.96 g, 8 mmol) in DMSO (10 ml) is added sodium hydride (0.14 g, 6 mmol) and the reaction mixture is stirred at 40° C. for 30 minutes. 5-chloro-7-[(R,S)-1,1,1-trifluoroprop-2ylamino )-6-(2,4,6-trifluorophenyl)-1,2,4-triazolo[1,5a]pyrimidine (0.79 g, 2 mmol, obtainable according to WO 98/45507) is added and the reaction mixture is heated in an oil bath (90° C.) over night with stirring. After cooling the reaction mixture to ambient temperature hydrochloric acid (1 N, 10 ml) and toluene (10 ml ) are added and the mixture is stirred vigorously for 10 minutes. The aqueous phase is separated and discarded. The organic layer is washed with water and brine, dried (MgSO4) and evaporated in vacuo to yield an oily residue which is crystallized from diisopropyl ether. 0.82 g of colorless crystals are obtained which have a melting point of 96° C.

EXAMPLES 5–47

The following examples (Table I; structure and melting point) are synthesized analogously to Examples 3 or 4.

TABLE I

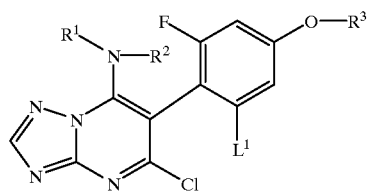

| Example | R$^1$ | R$^2$ | R$^3$ | L$^1$ | melting point (° C.) |
|---|---|---|---|---|---|
| 5 | isopropyl | H | methyl | F | 148 |
| 6 | 2,2,2-trifluoroethyl | H | methyl | F | 193 |
| 7 | (R,S)-1,1,1-trifluoroprop-2-yl | H | methyl | F | 167 |
| 8 | (S)-1,1,1-trifluoroprop-2-yl | H | methyl | F | 146 |

TABLE I-continued

| Example | R¹ | R² | R³ | L¹ | melting point (° C.) |
|---------|----|----|----|----|----------------------|
| 9 | H | H | methyl | F | 253 |
| 10 | (R)-1,1,1-trifluoroprop-2-yl | H | methyl | F | 145 |
| 11 | (R,S)-1,1,1-trifluoroprop-2-yl | H | ethyl | F | 158 |
| 12 | cyclopentyl | H | methyl | F | 144–148 |
| 13 | ethyl | ethyl | methyl | F | 100–104 |
| 14 | but-2-yl | H | methyl | F | 127–133 |
| 15 | —CH$_2$—CH=CH—(CH$_2$)$_2$— | | methyl | F | 118–123 |
| 16 | —(CH$_2$)$_2$—O—(CH$_2$)$_2$— | | methyl | F | 157–162 |
| 17 | —(CH$_2$)$_2$—S—(CH$_2$)$_2$— | | methyl | F | 166–170 |
| 18 | —(CH$_2$)$_6$— | | methyl | F | 166–171 |
| 19 | 1,2,2-trimethylpropyl | H | methyl | F | 179–183 |
| 20 | 2-methylallyl | ethyl | methyl | F | 101–105 |
| 21 | —(CH$_2$)$_2$—CH(CH$_3$)—(CH$_2$)$_2$— | | methyl | H | 143 |
| 22 | —(CH$_2$)$_2$—CH(CHOH)—(CH$_2$)$_2$— | | methyl | F | oil |
| 23 | —(CH$_2$)$_2$—CH(CHF)—(CH$_2$)$_2$— | | methyl | F | |
| 24 | 2,2,2-trifluoroethyl | H | methyl | H | |
| 25 | (S)-1,1,1-trifluoroprop-2-yl | H | methyl | H | |
| 26 | (R,S)-1,1,1-trifluoroprop-2-yl | H | ethyl | H | |
| 27 | cyclopentyl | H | methyl | H | |
| 28 | —(CH$_2$)$_6$— | | methyl | H | |
| 29 | —CH$_2$—CH=CH—(CH$_2$)$_2$— | | methyl | H | |
| 30 | (R,S)-1,1,1-trifluoroprop-2-yl | H | 2-fluoroethyl | F | semisolid |
| 31 | (R,S)-1,1,1-trifluoroprop-2-yl | H | 3-methylbut-2-enyl | F | 69 |
| 32 | (R,S)-1,1,1-trifluoroprop-2-yl | H | 2-methylbut-3-enyl | F | 85 |
| 33 | (R,S)-1,1,1-trifluoroprop-2-yl | H | 3-methylbutyl | F | 96 |
| 34 | (R,S)-1,1,1-trifluoroprop-2-yl | H | neopentyl | F | 85 |
| 35 | (R,S)-1,1,1-trifluoroprop-2-yl | H | 2-methoxyethyl | F | 170 |
| 36 | (R,S)-1,1,1-trifluoroprop-2-yl | H | 2-methoxypropyl | F | semisolid |
| 37 | (R,S)-1,1,1-trifluoroprop-2-yl | H | but-2-enyl | F | semisolid |
| 38 | (R,S)-1,1,1-trifluoroprop-2-yl | H | 2,2,2-trifluoro-ethyl | F | 77 |
| 39 | (R,S)-1,1,1-trifluoroprop-2-yl | H | benzyl | F | 146 |
| 40 | (R,S)-1,1,1-trifluoroprop-2-yl | H | 2-(2-ethoxy-ethoxy)-ethyl | F | 88 |
| 41 | isopropyl | H | ethyl | F | 142 |
| 42 | 2-methylallyl | ethyl | ethyl | F | 112–114 |
| 43 | —(CH$_2$)$_6$— | | ethyl | F | 115 |
| 44 | (R,S)-1,1,1-trifluoroprop-2-yl | H | methyl | Cl | 146–148 |
| 45 | (R,S)-1,1,1-trifluoroprop-2-yl | H | allyl | F | 100 |
| 46 | (R,S)-1,1,1-trifluoroprop-2-yl | H | 2,2-difluoroethyl | F | 173 |
| 47 | (R,S)-1,1,1-trifluoroprop-2-yl | H | n-butyl | F | 87–88 |

Biological Investigations
Determination of Minimum Inhibitory Concentration by Test Compounds in the Serial Dilution Test The MIC (Minimum Inhibitory Concentration) value, which indicates the lowest concentration of the active ingredient in the growth medium which causes a total inhibition of mycelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 (alternatively a starting concentration of and 100.00 µg/ml (alternatively a starting concentration of 5.00 ppm with 12 serial dilutions were used). For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The respective inocula (*Alternaria solani*, ALTESO; *Botrytis cinerea*, BOTRCI; *Cochliobulus sativus*, COCHSA; *Leptosphaeria nodorum*, LEPTNO; *Magnaporthe grisea* f sp. Oryzae, PYRIOR; *Rhizoctonia solani*, RHIZSO; are added into the wells as spore suspensions (50 ml; 5×10$^5$/ml) or agar slices (6 mm) of an agar culture of the fungus. After 6–12 days incubation at suitable temperatures (18–25° C.), the MIC values are determined by visual inspection of the plates (Table II; n.t.=not tested).

TABLE II

| Ex. No. | ALTESO | BOTRCI | COCHSA | LEPTNO | PYRIOR | RHISZO |
|---|---|---|---|---|---|---|
| 3 | <0.05 | 0.2 | 0.39 | 1.56 | <0.05 | >100 |
| 5 | 0.78 | 1.56 | 6.25 | 6.25 | 0.2 | 6.25 |
| 6 | 0.39 | 0.78 | 6.25 | 6.25 | <0.05 | 6.25 |
| 7 | 0.2 | 0.2 | 1.56 | 1.56 | <0.05 | 3.13 |
| 8 | 0.078 | 0.2 | 1.56 | 1.25 | 0.02 | 1.25 |
| 9 | 0.78 | 0.78 | 50 | 25 | 1.56 | 25 |
| 10 | 0.78 | 0.39 | 3.13 | 12.5 | <0.05 | 3.13 |
| 11 | 0.1 | 0.1 | 3.13 | 1.56 | 0.2 | 6.25 |
| 12 | 0.1 | 0.39 | 1.56 | 1.56 | 0.1 | 25 |
| 13 | 0.78 | 3.13 | 3.13 | 3.13 | <0.05 | 6.25 |
| 14 | 0.78 | 1.56 | 3.13 | 3.13 | <0.05 | 6.25 |
| 15 | <0.05 | 0.78 | 0.78 | 3.13 | <0.05 | 100 |
| 16 | 0.39 | 6.25 | 3.13 | 6.25 | 0.39 | 12.5 |
| 17 | 0.1 | 3.13 | 0.78 | >100 | 0.1 | 25 |
| 18 | 0.1 | 0.78 | 0.78 | 3.13 | 0.1 | 50 |
| 19 | <0.05 | 3.13 | 0.39 | 6.25 | 0.4 | >100 |
| 20 | <0.05 | 0.1 | 0.39 | 0.78 | 0.4 | 0.2 |
| 21 | 0.10 | 0.78 | 1.56 | 6.25 | <0.05 | >100 |
| 30 | <0.05 | 0.39 | 1.56 | 1.56 | <0.05 | 100 |

What is claimed is:

1. A compound of formula I

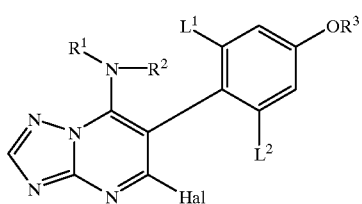

(I)

in which
R$^1$ represents straight chain or branched C$_1$–C$_6$ alkyl, C$_2$–C$_6$ alkenyl, or C$_1$–C$_6$ haloalkyl;
R$^2$ represents hydrogen or straight chain or branched C$_1$–C$_6$ alkyl; or,
R$^1$ and R$^2$ together with the interjacent nitrogen atom represent a heterocyclic ring optionally substituted with one or two C$_1$–C$_6$ alkyl groups wherein the heterocyclic ring atoms consist of the interjacent nitrogen atom and 5–6 carbon atoms;
R$^3$ represents C$_3$–C$_6$ alkenyl, C$_3$–C$_6$ alkynyl, phenyl-C$_1$–C$_6$alkyl, C$_1$–C$_4$ alkoxy-C$_1$–C$_4$ alkyl, di-C$_1$–C$_4$ alkoxy-C$_1$–C$_4$ alkyl, phenyl or C$_1$–C$_4$ haloalkyl group;
L$^1$ represents a hydrogen, fluorine or chlorine atom;
L$^2$ represents a fluorine or chlorine atom; and
Hal represents a halogen atom.

2. A compound according to claim 1 in which, and L$^1$ and L$^2$ each represent a fluorine atom.

3. A compound according to claim 1 in which R$^2$ represents a hydrogen atom.

4. A compound according to claim 1 in which R$^1$ and R$^2$ together with the interjacent nitrogen atom represent a heterocyclic ring selected from 4-methylpiperidin-1-yl, 2-methylpiperidin-1-yl, 5,6-dihydro-2H-pyridin-1-yl, 2-ethylpiperidin-1-yl and azepan-1-yl.

5. A compound of formula I according to claim 1 selected from the group consisting of:
   5-chloro-7-[N-2-(1,1,1-trifluoropropyl)-amino]-6-(2,6-difluoro-4-(2-fluoroethoxy)-phenyl)-[1,2,4]triazolo[1,5-a]pyrimidine,
   5-chloro-7-[N-2-(1,1,1-trifluoropropyl)-amino]-6-(2,6-difluoro-4-(3-methylbut-2-enyloxy)-phenyl)-[1,2,4]triazolo[1,5-a]pyrimidine,
   5-chloro-7-[N-2-(1,1,1-trifluoropropyl)-amino]-6-(2,6-difluoro-4-(2-methylbut-3-enyloxy)-phenyl)-[1,2,4]triazolo[1,5-a]pyrimidine,
   5-chloro-7-[N-2-(1,1,1-trifluoropropyl)-amino]-6-(2,6-difluoro-4-benzyloxyphenyl)-[1,2,4]triazolo[1,5-a]pyrimidine,
   5-chloro-7-[N-2-(1,1,1-trifluoropropyl)-amino]-6-(2,6-difluoro-4-[2-(2-ethoxy-ethoxy)-ethoxy]-phenyl)-[1,2,4]triazolo[1,5-a]pyrimidine,
   5-chloro-7-[N-2-(1,1,1-trifluoropropyl)-amino]-6-(2,6-difluoro-4-[2-(2-methoxy-ethoxy)-ethoxy]-phenyl)-[1,2,4]triazolo[1,5-a]pyrimidine,
   5-chloro-7-[N-2-(1,1,1-trifluoropropyl)-amino]-6-(2,6-difluoro-4-(2-methoxyethoxy)-phenyl)-[1,2,4]triazolo[1,5-a]pyrimidine,
   5-chloro-7-[N-2-(1,1,1-trifluoropropyl)-amino]-6-(2,6-difluoro-4-(2-methoxypropoxy)-phenyl)-[1,2,4]triazolo[1,5-a]pyrimidine,
   5-chloro-7-[N-2-(1,1,1-trifluoropropyl)-amino]-6-(2,6-difluoro-4-but-2-enyloxyphenyl)-[1,2,4]triazolo[1,5-a]pyrimidine, and
   5-chloro-7-[N-2-(1,1,1-trifluoropropyl)-amino]-6-(2,6-difluoro-4-(2,2,2-trifluoroethoxy)-phenyl)-[1,2,4]triazolo[1,5-a]pyrimidine.

6. A process for the preparation of a compound of formula I as defined in claim 1 which comprises treating a compound of formula II

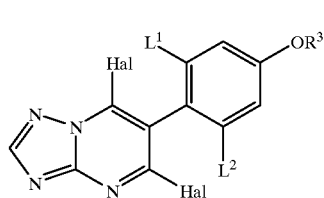

(II)

in which
R$^3$, L$^1$, L$^2$ and Hal are as defined in claim 1, with an amine of formula III

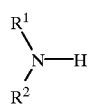 (III)
in which R¹ and R² are as defined in claim 1.
7. A fungicidal composition which comprises a carrier, and as active agent, at least one compound of formula I as defined in claim 1.
8. A method of combating fungus at a locus which comprises treating the locus with an effective amount of least one compound of formula I as defined in claim 1.
\* \* \* \* \*